(12) United States Patent
Atkinson et al.

(10) Patent No.: US 8,436,299 B2
(45) Date of Patent: *May 7, 2013

(54) DETECTION APPARATUS

(75) Inventors: Johnathan Richard Atkinson, Watford (GB); Alastair Clark, Watford (GB); Stephen John Taylor, Hyde Heath (GB); William Angus Munro, Watford (GB)

(73) Assignee: Smiths Detection—Watford Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/094,592

(22) Filed: Apr. 26, 2011

(65) Prior Publication Data

US 2011/0284739 A1    Nov. 24, 2011

Related U.S. Application Data

(63) Continuation of application No. 11/918,940, filed as application No. PCT/GB2006/001442 on Apr. 20, 2006, now Pat. No. 7,932,489.

(30) Foreign Application Priority Data

Apr. 23, 2005   (GB) .................................. 0508239.1

(51) Int. Cl.
  *H01J 49/40*   (2006.01)
(52) U.S. Cl.
  USPC ........................................................ 250/287

(58) Field of Classification Search .................... 250/287
See application file for complete search history.

(56) References Cited

U.S. PATENT DOCUMENTS

| 4,551,624 | A | * | 11/1985 | Spangler et al. ............... 250/287 |
| 5,245,192 | A |   | 9/1993  | Houseman |
| 5,338,931 | A | * | 8/1994  | Spangler et al. ............... 250/287 |
| 6,323,482 | B1 |  | 11/2001 | Clemmer et al. |
| 6,690,004 | B2 |  | 2/2004  | Miller et al. |
| 6,949,743 | B1 |  | 9/2005  | Schwartz |
| 7,019,286 | B2 |  | 3/2006  | Fuhrer et al. |
| 7,129,482 | B2 |  | 10/2006 | Miller et al. |
| 7,932,489 | B2 | * | 4/2011  | Atkinson et al. ............... 250/287 |
| 2002/0014586 | A1 | | 2/2002 | Clemmer |
| 2003/0209665 | A1 | | 11/2003 | Losch et al. |
| 2004/0032211 | A1 | | 2/2004 | Langford et al. |

FOREIGN PATENT DOCUMENTS

| WO | WO-00/79261 A1 | 12/2000 |
| WO | WO 00/79261 A1 * | 12/2000 |
| WO | WO-2004/097396 A1 | 11/2004 |

* cited by examiner

*Primary Examiner* — Jack Berman
(74) *Attorney, Agent, or Firm* — Foley & Lardner LLP

(57) ABSTRACT

An ion mobility spectrometer has a pair of electrodes and midway along the drift chamber. A high field is applied between the electrodes and sufficient to modify ions in the region of thee electrodes such that they move at a different rate towards the collector plate. This is used to modify the time of flight of selected ions or ion clusters and enable identification of ambiguous peaks on the IMS spectrum.

19 Claims, 1 Drawing Sheet

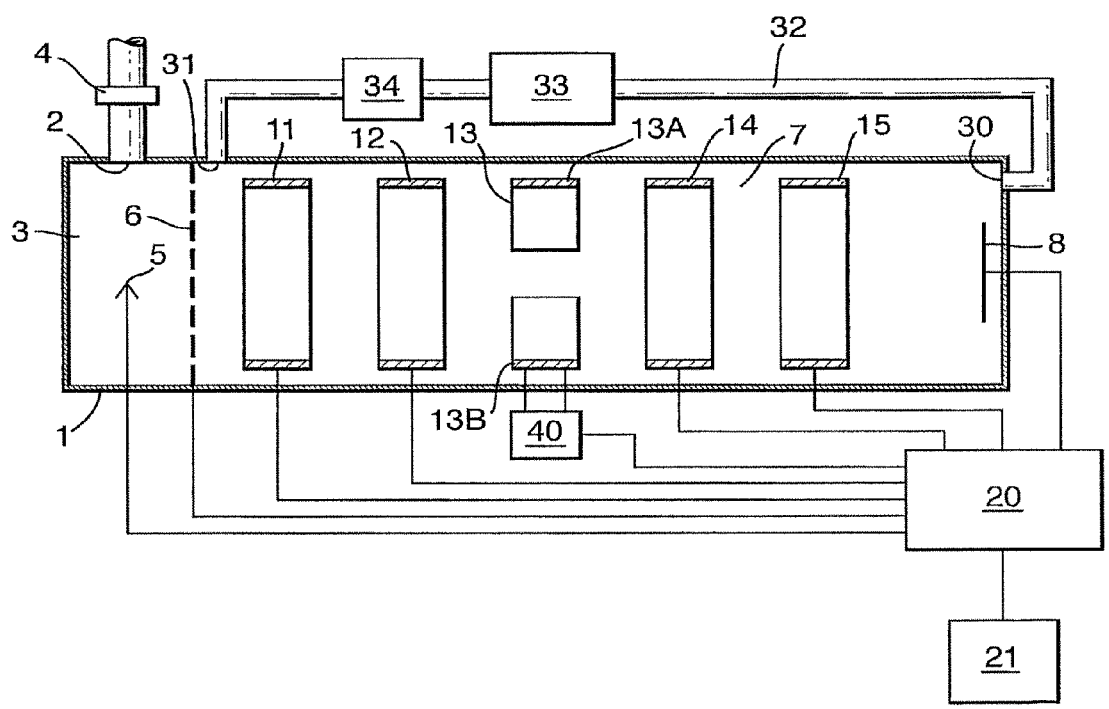

DETECTION APPARATUS

This invention relates to detection apparatus of the kind for detecting substances in a sample.

The invention is more particularly, but not exclusively concerned with ion mobility spectrometers (IMSs).

Ion mobility spectrometers (IMSs) are used to detect the presence of small quantities of airborne chemicals in vapours or gases at atmospheric pressure. An IMS has some means to ionize the sample chemicals, such as a corona discharge or a radioactive source. A gate is opened to admit the molecular ion clusters into one end of a drift chamber across which a voltage is applied to cause the ion clusters to drift to the opposite end where they are collected on a collector plate. The molecular ion clusters might also include attached dopant ions. The time taken for a molecular ion cluster to pass from the gate to the collector plate is dependent on the mass, size, shape and charge on the molecular ion cluster. By measuring this time an indication can be provided of the nature of the chemical.

In many cases it can be difficult to identify positively the substance of interest because the time of flight of the ion clusters produced may be very similar to that of ion clusters of different substances. Various arrangements have been proposed for improving the discrimination between different molecular ion clusters. One arrangement described in U.S. Pat. No. 6,797,943 involves fragmenting the ions using laser energy, a pyrolyzer or the like. The ion clusters are accumulated in a reservoir where they are exposed to the ion modification energy prior to admittance to the drift chamber. One problem with this arrangement is that all the molecular ion clusters are subjected to fragmentation, which can lead to a large number of peaks on the spectrum, making analysis very difficult. Another problem with this arrangement is that a relatively large amount of energy is needed to ensure that fragmentation takes place, which can be a particular problem in portable, battery-powered apparatus.

It is an object of the present invention to provide alternative detection apparatus.

According to one aspect of the present invention there is provided detection apparatus of the above-specified kind, characterised in that the apparatus includes an electrical arrangement for subjecting molecules of the substances to an electrical field high enough to cause ion modification of some at least of the molecules.

The apparatus preferably includes an ionizer for ionizing the sample and an arrangement for measuring the mobility of the ions produced, the electrical arrangement causing ion modification of some at least of the ionized molecules. The electric field is preferably symmetrical and could be an RF field. The electric field could be applied in short bursts. The molecules may be individual molecules or clusters of molecules and may include attached dopant molecules. The electrical field may be arranged to cause modification of only selected ones of the molecules.

According to another aspect of the present invention there is provided detection apparatus for detecting substances in a sample, characterised in that the apparatus includes an arrangement for applying energy to molecules of the substance sufficient to cause ion modification of only selected ones of the molecules.

According to a further aspect of the present invention there is provided detection apparatus for detecting substances in a sample, characterised in that the apparatus is arranged to separate out molecules of different substances from one another into different regions of the apparatus and that the apparatus includes an arrangement for applying energy to a selected one of the regions sufficient to cause ion modification of only those molecules in that region.

According to a fourth aspect of the present invention there is provided ion mobility spectrometer apparatus including an ionization region, a gate, a drift chamber and a collector, characterised in that the apparatus includes a pair of electrodes spaced from one another across the apparatus, and that the apparatus is arranged to apply a high field between the electrodes sufficient to modify ions such that the modified ions travel at a different speed to the collector from unmodified ions.

The pair of electrodes may be located in the drift chamber. The apparatus may be arranged to apply the high field between the electrodes a predetermined time after opening the gate so that only ions with a selected range of mobilities are modified by the high field.

According to a fifth aspect of the present invention there is provided a method of detecting substances in a sample including the steps of applying energy to modify only selected molecules of the substances prior to detection.

The energy may be applied at times selected preferentially to cause ion modification of ions having selected ranges of mobility. The energy is preferably applied for short periods of time and/or at high frequency. The energy is preferably applied by means of an electrical field.

A time-of-flight ion mobility spectrometer according to the present invention will now be described, by way of example, with reference to the accompanying drawing, which shows the spectrometer schematically.

BRIEF DESCRIPTION OF THE DRAWINGS

FIG. 1 Illustrates an embodiment of an ion mobility spectrometer.

DESCRIPTION

The spectrometer includes an elongate, tubular housing 1 the interior of which is substantially at atmospheric pressure. An inlet port 2 towards its left-hand end opens into an ionisation region 3. A sample gas or vapour to be analysed is supplied to the port 2 via a filter 4, in the conventional manner. The ionisation region 3 includes a corona discharge point 5 or some other means, such as a radioactive source, for ionising the sample. A gate 6 separates the ionisation region 3 from a drift chamber 7, which extends to the right-hand end of the housing 1 where an ion collector plate 8 is mounted. The drift chamber 7 includes a row of electrodes 11 to 15 spaced from one another along the length of the drift chamber 7 in the usual way. The collector plate 8, electrodes 11 to 15, gate 6 and discharge point 5 are electrically connected to a processor control unit 20, which provides an output to a display or other utilisation unit 21 representative of the substances detected.

Drift gas is supplied to the right-hand end of the housing 1 at an inlet 30 to flow from right to left along the drift chamber 7, that is, in the opposite direction from the flow of ions. Drift gas is exhausted from the drift chamber 7 at its left-hand end through an outlet port 31.

Gas flows between the outlet port 31 and the inlet 30 via a gas system 32, which includes a molecular sieve 33 and a pump 34. The sieve 33 may contain a dopant in the manner described in W000/79261. Ions produced in the ionisation region 3 are admitted into the left-hand end of the drift chamber 7 when the gate 6 is opened. The ions drift from left to right along the drift chamber under the influence of the relatively low electrical field of about 250 V cm-1 applied by the electrodes 11 to 15. The ions of different mobilities separate out from one another as they pass along the drift chamber 7 so that, at anyone time, different ions will be in different regions of the chamber. The ions of different mobilities, therefore, reach the collector plate 8 at different times and produce output peaks to the processing unit 20 at different times.

As so far described, the apparatus is conventional.

The apparatus differs from previous apparatus by the inclusion of means to apply a high electrical field to cause ion modification of the ions, such as fragmentation. There are various ways in which this could be achieved. The high field could be applied at any part of the apparatus, but, in the present example, it is applied in the drift chamber 7. The field is applied by means of the electrode 13, which is separated into two electrodes 13A and 13B spaced from one another across the diameter of the drift chamber 7. Although these electrodes 13A and 13B are shown midway along the drift chamber 7, they could be located at any point along the chamber. These electrodes 13A and 13B are connected to a high voltage RF unit 40 controlled by the processing unit 20. The high voltage unit 40 is operable to apply a high strength RF field (typically around 2 MHz) effective to cause ion modification of a significant percentage of the ions within the field. The strength of the field is preferably at least 10,000V/cm and may be of the order of several tens of thousands of volts per centimeter. The RF field may be applied continuously or in bursts of the order of 1 μs in order to prevent corona discharge. The symmetrical nature of the applied field is advantageous because it ensures that the molecular ion clusters remain substantially central within the drift chamber 7 and are not displaced to contact with the electrodes 13 to 15. Alternatively, non-RF intense short pulses of the order of 1 ns could be used. These fields enable sufficient energy to be transferred to the ions to cause ion modification. The modified or fragmented ions pass to the collector plate 8 with a different mobility from the unmodified ions and hence produce different peaks on the output spectrum. This can enable the apparatus to distinguish between two different ions having similar mobilities, since the modified versions of these ions will not generally have similar mobilities.

The sample gas or vapour could include a dopant selected to stabilise the neutral molecule environment in the device, such as water at a few hundred ppm.

The apparatus could be arranged to operate conventionally most of the time with the two electrodes 13A and 13B being at the same dc voltage, between the voltages on adjacent electrodes 12 and 14, that is, without the ion modification field. When an ambiguous substance is identified, the processing unit 20 would initiate the ion modification field in order to resolve the ambiguity. Alternatively, the apparatus could be operated with the ion modification field continuously on and then turn it off for short periods to confirm detection of a substance.

Application of the ion modification field could be coupled to operation of the gate 6. In such an arrangement, the ion modification field is initiated at a calculated predetermined time after opening the gate 6 such that only those ions within a selected range of mobilities are in the region of the ion modification field electrodes 13A and 13B when they are energized with the ion modification voltage. This arrangement helps confine the ion modification process to selected ions only, thereby avoiding too many peaks being produced on the spectrum and facilitating identification.

Alternative energy sources could be used to produce ion modification on selected ionized molecules in a similar manner. Such alternative energy sources could include: radiation sources, such as laser radiation, UV radiation, VUV radiation, infra-red or photo ionisation, electron bombardment, electron beams, electro spray, electron-ionisation, corona discharge, glow discharge, plasma or radioactive emission.

The ion modification field could be applied at any location, such as in the ionization region 3 or at the gate 6 and could be applied at any time during each scan of the IMS apparatus. The invention could be applied to detection apparatus other than IMS apparatus.

The invention claimed is:

1. A detector, comprising:
   an ionizer;
   a collector plate; and
   a drift chamber;
   wherein the drift chamber comprises:
     at least one first electrode pair for causing ions to move to the collection plate, and
     an ion modifier disposed in the drift chamber, the ion modifier configured to modify ion mobilities of respective ones of the ions.

2. The detector of claim 1, wherein the ion modifier comprises a second electrode pair.

3. The detector of claim 1, wherein the at least one first electrode pair comprises a plurality of electrode pairs, and the ion modifier is disposed between two of the electrode pairs.

4. The detector of claim 1, wherein the detector is portable.

5. The detector of claim 1, further comprising a sieve which contains a dopant.

6. The detector of claim 1, wherein the ion modifier comprises a second electrode pair connected to a high voltage RF unit.

7. The detector of claim 1, further comprising an arrangement for measuring the mobility of at least ions modified by the ion modifier.

8. The detector of claim 1, wherein the at least one first electrode pair is configured to provide a symmetrical electrical field.

9. A method of detecting components in a sample, comprising:
   producing, during a gate open period, sample ions from a corona discharge;
   admitting at least some of the produced ions into a drift chamber;
   applying, in the drift chamber, a first field to cause admitted ions to move to a collection plate;
   applying, in the drift chamber, a second field to modify at least some of the admitted ions;
   wherein the first and second fields are different.

10. The method of claim 9, wherein the second field is formed between electrodes disposed in the drift chamber.

11. The method of claim 9, wherein the second field is initiated at a predetermined time after the gate is opened so only those ions in a selected range of ion mobilities are modified.

12. The method of claim 10, wherein the second field transfers energy to some of the admitted ions having a predetermined mobility range, sufficient to modify ions in the predetermined mobility range.

13. The method of claim 9, further comprising providing the admitted ions to the collector plate, wherein modified ions reach the collector plate at different times than unmodified ions after the at least some of the produced ions are admitted into the drift chamber.

14. The method of claim 9, wherein the second field is an RF field.

15. The method of claim 9, wherein the second field is at least 10,000 V/cm.

16. The method of claim 9, wherein the second field is applied continuously.

17. The method of claim 9, further comprising measuring mobility of at least the modified ions.

18. The method of claim 9, wherein the modified ions arrive at the collector plate as fragmented ions, the mobility of the fragmented ions and mobility of unmodified ions is different.

19. The method of claim 9, wherein the sample ions are produced from individual molecules or clusters of molecules.

* * * * *